United States Patent [19]

Thibault et al.

[11] 4,345,936
[45] Aug. 24, 1982

[54] IMIDAZOLES, COMPOSITIONS AND HERBICIDAL METHOD

[75] Inventors: Thomas D. Thibault, Indianapolis; Roger L. St. Clair, Greenfield, both of Ind.

[73] Assignee: Eli Lilly and Company, Indianapolis, Ind.

[21] Appl. No.: 308,728

[22] Filed: Oct. 5, 1981

[51] Int. Cl.³ .................. A01N 43/50; C07D 233/68; C07D 233/78; C07D 233/86
[52] U.S. Cl. .......................................... 71/92; 71/76; 424/273 R; 548/319
[58] Field of Search ............................. 548/319; 71/92

[56] References Cited

U.S. PATENT DOCUMENTS

| | | | |
|---|---|---|---|
| 3,216,816 | 9/1965 | Luckenbaugh | 71/2.5 |
| 3,822,282 | 7/1974 | Singer | 260/309.5 |
| 3,923,827 | 12/1975 | Dixon et al. | 260/309.6 |
| 3,925,553 | 12/1975 | Singer | 424/273 |
| 4,036,850 | 7/1977 | Enders | 260/309.5 |
| 4,248,620 | 2/1981 | Singer | 71/92 |

FOREIGN PATENT DOCUMENTS

| | | |
|---|---|---|
| 743708 | 12/1969 | Belgium . |
| 3619 | 8/1979 | European Pat. Off. . |
| 1039302 | 9/1958 | Fed. Rep. of Germany . |
| 2065977 | 8/1977 | Fed. Rep. of Germany . |
| 6902608 | 2/1968 | Netherlands . |
| 1247397 | 9/1971 | United Kingdom . |

OTHER PUBLICATIONS

Derwent Abstract Nos. 33439Y, Mar. 28, 1977, 38201W, Jan. 27, 1973.

Primary Examiner—Robert W. Ramsuer
Attorney, Agent, or Firm—Charles W. Ashbrook; Arthur R. Whale

[57] ABSTRACT

There is disclosed substituted 2,3-dihydro-2-oxo-1H-imidazole-4-carboxaldehyde derivatives of the formula

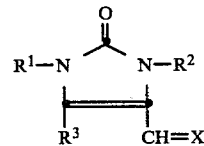

in which $R^1$ and $R^2$ independently are alkyl or mono or di-substituted phenyl, $R^3$ is chloro, alkoxy, alkylthio, or $NR^4R^5$ in which $R^4$ and $R^5$ are alkyl or alkenyl, and X is O or N-alkyl. The compounds are herbicides.

33 Claims, No Drawings

IMIDAZOLES, COMPOSITIONS AND HERBICIDAL METHOD

BACKGROUND OF THE INVENTION

This invention concerns 2,3-dihydro-2-oxo-1H-imidazole-4-carboxaldehyde derivatives. The compounds are useful as herbicides.

Several imidazole derivatives which allegedly have herbicidal activity are known in the art.

U.S. Pat. No. 4,036,850 discloses a group of 1-aryl-5-alkylidene-2,4-imidazolidinediones which are said to be active as herbicides, fungicides, bactericides, nematocides, as well as coccidiostats. German Pat. No. 1,039,302 describes a group of herbicidal 2,4-imidazolidinediones which are unsubstituted at the 5-position. U.S. Pat. Nos. 3,822,282 and 3,925,553 describe a series of 2,4-imidazolidine-diones which require a polyhaloethylimine or a polyhalovinylimine group at the imidazolidine 5-position. Such compounds are said to be valuable herbicidal and fungicidal agents. A group of 5-carbamoylimino-2,4-imidazolidinediones which are allegedly useful as herbicides is disclosed in British Pat. No. 1,247,397.

SUMMARY OF THE INVENTION

This invention provides a group of 5-substituted 2,3-dihydro-2-oxo-1H-imidazole-4-carboxaldehyde derivatives which are useful as herbicides. The invention is more particularly directed to 2-oxo-imidazoles defined by the formula

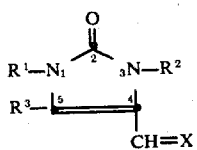

wherein:

$R^1$ and $R^2$ independently are lower alkyl, cycloalkyl, phenyl, or phenyl substituted with one or two groups selected from halo, lower alkyl, lower alkoxy, halo lower alkyl, or nitro;

$R^3$ is chloro, lower alkoxy, lower alkylthio, or $NR^4R^5$, in which $R^4$ is methyl or ethyl and $R^5$ is methyl, ethyl, or propenyl;

and X is O or N-lower alkyl.

Preferred compounds provided by the invention are those wherein X is O or N—$CH_3$, especially those wherein X is O. Also preferred are those wherein $R^1$ is phenyl or mono-substituted phenyl and $R^2$ is methyl.

Also preferred are compounds wherein $R^3$ is $NR^4R^5$ and $R^4$ and $R^5$ both are methyl.

A particularly preferred group of compounds are defined by the above formula wherein $R^1$ is phenyl, 3-chlorophenyl, 4-chlorophenyl, 3-methylphenyl, 4-methylphenyl, 3-nitrophenyl, 4-methoxyphenyl or 3-trifluoromethylphenyl; $R^2$ is methyl, X is O or N—$CH_3$, and $R^3$ is $N(CH_3)_2$.

Also provided by this invention are agricultural compositions comprising an imidazolecarboxaldehyde derivative of the above formula together with a suitable agronomic carrier therefor.

A further embodiment of this invention is a method for controlling unwanted vegetative growth comprising applying to the locus where vegetative control is desired an effective amount of a compound defined by the above formula.

Additionally provided by this invention is a process for preparing the imidazoles defined above wherein $R^3$ is chloro and X is oxygen. The new process comprises reacting an aminomethylene imidazolidinedione with phosphorus oxychloride.

DETAILED DESCRIPTION OF THE INVENTION

The compounds of this invention will be referred to generically herein as "imidazole carboxaldehyde derivatives". The term includes compounds of the above formula wherein X is oxygen, which are carboxaldehydes per se, and compounds wherein X is N-lower alkyl, which are derivatives of the carboxaldehydes.

As used herein, the term "lower alkyl" refers to groups such as methyl, ethyl, n-propyl, isopropyl, n-butyl, iso-butyl, tert-butyl, n-pentyl, n-hexyl and the like. "Lower alkoxy" includes groups such as methoxy, ethoxy, n-propoxy, isobutoxy, tert-butoxy, n-pentyloxy and the like. "Lower alkylthio" refers to groups such as methylthio, ethylthio, n-propylthio, n-butylthio, 1-methylbutylthio, n-hexylthio and the like. "Halo" as used herein includes chloro, fluoro, bromo and iodo. "Halo lower alkyl" groups thus include the above defined lower alkyl groups substituted with one or more halo groups. Typical halo lower alkyl groups include chloromethyl, 2-bromoethyl, 4-fluorobutyl, dibromomethyl, trifluoromethyl and the like.

$R^1$ and $R^2$ in the above formula independently can be lower alkyl, cycloalkyl, phenyl or mono or disubstituted phenyl. Cycloalkyl groups include cyclopropyl, cyclobutyl, cyclopentyl, cyclohexyl and cycloheptyl. Substituted phenyl groups include halo phenyl such as 2-chlorophenyl, 4-iodophenyl, 3-fluorophenyl, 2,3-dibromophenyl, 3-bromo-4-chlorophenyl, 2,4-difluorophenyl, and the like. Typical lower alkyl phenyl groups include 2-methylphenyl, 3-ethylphenyl, 4-isopropylphenyl, 3-tert-butylphenyl, 2-ethyl-3-methylphenyl, and related groups. Alkoxyphenyl groups include 2-methoxyphenyl, 3-ethoxyphenyl, 4-n-butoxyphenyl, 3-methoxy-4-n-butoxyphenyl, 2,4-dimethoxyphenyl, 2,6-dimethoxyphenyl, and 2-sec-butoxyphenyl. Typical halo lower alkyl phenyl groups include 2-trifluoromethylphenyl, 3-bromomethylphenyl, 4-trichloromethylphenyl, 2,6-di-trifluoromethylphenyl, and related groups. Nitrophenyl groups include 2-nitrophenyl, 3-nitrophenyl, 3,4-dinitrophenyl and the like. Other typical substituted phenyl groups include 2-chloro-4-methoxyphenyl, 3-ethoxy-4-nitrophenyl, 2-trifluoromethyl-4-tert.-butylphenyl, 3-methyl-6-sec-butylphenyl and 3-n-propoxy-4-tert-butylphenyl.

The 5-substituted 2,3-dihydro-2-oxo-1H-imidazole-4-carboaldehydes provided by this invention, i.e. compounds wherein X in the above formula is O, can be prepared by one of two alternative procedures, one which is novel and the other which is analogous to art known synthetic processes.

According to the novel procedure, which is provided as a further embodiment of the present invention, phosphorus oxychloride is reacted with an appropriately 1,3-disubstituted-5-(dialkylamino)methylene-2,4-imidazolidinedione in the presence of an aprotic solvent such as N,N-dimethylformamide (DMF) to give a 5- chloro-1,3-disubstituted-2,3-dihydro-2-oxo-1H-imidazole-4-carboxaldehyde of the invention. The 5-chloro imidazoles thus prepared are valuable as herbicides, and also can be reacted with a secondary amine by known processes to give the 5-amino-dihydro-imidazole carboxaldehydes of the invention. This over-all synthetic sequence can be illustrated by the following general scheme:

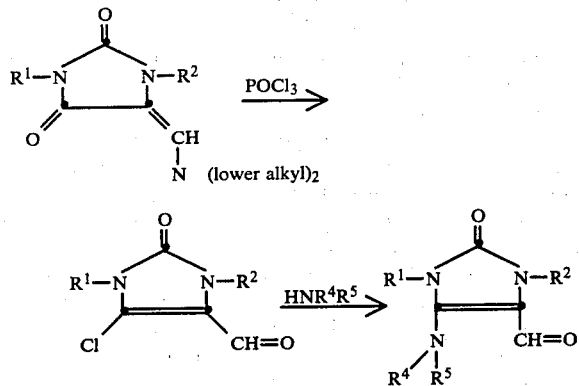

In the above scheme, $R^1$, $R^2$, $R^4$, $R^5$ and "lower alkyl" are as defined above. The (dialkylamino)-methylene-2,4-imidazolidinediones which are employed as starting materials in the above sequence are the subject of Thibault's copending application Ser. No. 308,621 filed even date herewith.

The (dialkylamino)methylene-2,4-imidazolidinedione which is the required starting material can be prepared by reaction of a 5-unsubstituted 2,4-imidazolidinedione with N,N-dialkylformamide dimethyl acetal. The 5-unsubstituted imidazolidinedione generally is derived by cyclization of a suitably substituted N-carbamoyl aminoacetic acid derivative, which in turn can be prepared by reaction of an isocyanate with an N-substituted amino-acetic acid derivative. This over-all reaction sequence is depicted by the following general scheme:

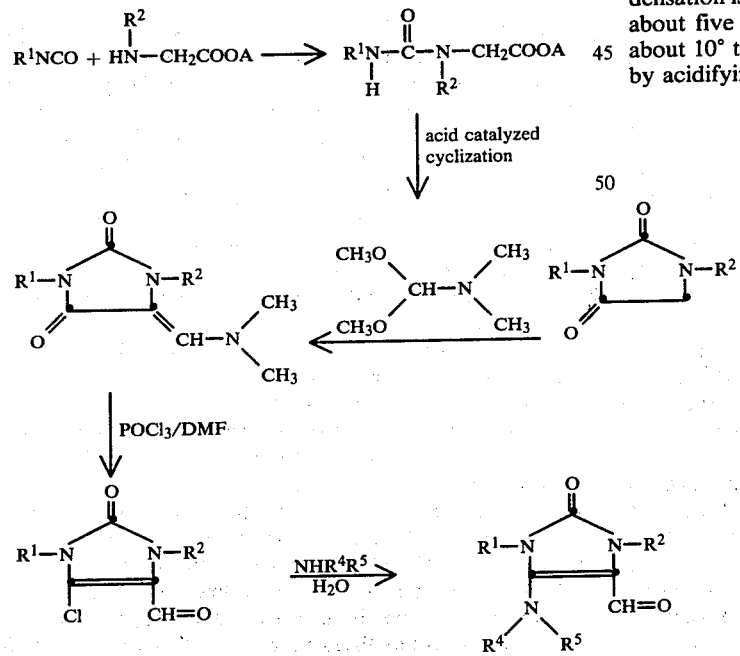

In the above scheme, $R^1$, $R^2$, $R^4$ and $R^5$ are as defined above, and A is hydrogen or lower alkyl such as methyl or ethyl.

The 5-chloro substituted 2,3-dihydro-2-oxo-1H-imidazolecarboxaldehydes provided by the invention can alternatively be prepared directly from a 5-unsubstituted imidazolidinedione by procedures well known in the art that comprise reaction with phosphorus oxychloride and dimethylformamide. This reaction is depicted as follows:

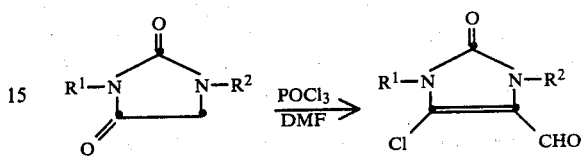

As mentioned above, the 5-chloro imidazoles of the invention are useful as herbicides, and additionally can be reacted with an amine to give the 5-amino imidazoles of the invention.

It will be notes that both processes leading to the 5-chloro imidazoles of this invention require a 2,4-imidazolidinedione as a starting material. As noted above, the 2,4-imidazolidinediones are prepared by cyclization of an N-carbamoyl aminoacetic acid derivative, which in turn is derived from an isocyanate and an N-substituted amino-acetic acid derivative.

The reaction of an isocyanate with an amino-acetic acid or ester to give the corresponding N-carbamoyl aminoacetic acid derivative, and the subsequent cyclization thereof to provide a 5-unsubstituted-2,4-imidazolidinedione, can be carried out by the general procedure described in German Pat. No. 1,039,302. for example, an isocyanate such as phenylisocyanate is reacted with about an equimolar amount or slight excess of an N-alkylaminoacetic acid such as N-ethyl aminoacetic acid. The reaction generally is carried out in an aqueous media and in the presence of a base such as sodium hydroxide or the like. The reaction can also be conducted in an organic solvent such as toluene. The condensation is generally complete after about two hours to about five days when carried out at a temperature of about 10° to about 100° C. The product can be isolated by acidifying the reaction mixture, for example by the addition of a mineral acid, which normally causes precipitation of the product. Filtration affords the corresponding N-carbamoyl aminoacetic acid derivative. When an organic solvent is employed, it generally is simply removed by evaporation.

The N-carbamoyl aminoacetic acid derivative is readily cyclized to a 5-unsubstituted-2,4-imidazolidinedione by simply heating so as to eliminate water, or an alcohol in the case of an aminoacetic acid ester. The cyclization preferably is catalyzed by an aqueous mineral acid such as hydrochloric acid or the like. The cyclization is normally complete within about two to about four hours when carried out at about 50° to about 150° C. The 5-unsubstituted imidazolidinedione can be isolated by simply adding the reaction mixture to ice and subsequently collecting the precipitated product by filtration. Purification by recrystallization from common solvents can be carried out if desired.

The 5-(dialkylamino)methylene-2,4-imidazolidinediones which are starting materials for the 5-chloroimidazoles prepared by the novel process of this invention are then prepared by reaction of the 5-unsubstituted-2,4-imidazolidinedione with an excess of an acetal of an N,N-dialkylformamide, for instance the dimethyl acetal of N,N-diethylformamide. The reaction generally is carried out by simply dissolving the 5-unsubstituted-2,4-imidazolidinedione in an excess of the dialkylformamide acetal and heating the reaction solvent to about 50° to about 100° C. for about eight to about forty-eight hours. The product of the reaction, a 5-(dialkylamino)methylene-2,4-imidazolidinedione, is readily isolated by cooling the reaction mixture to room temperature and then filtering the solid precipitate. Further purification normally is not required but can be accomplished if desired by conventional methods, including crystallization from common organic solvents such as ethyl acetate, diethyl ether, and the like. These 5-(dialkylamino)methylene-2,4-imidazolidinediones are also useful as herbicides and are the subject of copending application Ser. No. 308,621 filed Oct. 5, 1981.

Illustrative of the starting materials thus prepared are the following:

5-(dimethylamino)methylene-1-ethyl-3-(3-bromophenyl)-2,4-imidazolidinedione;
5-(diethylamino)methylene-1-isopropyl-3-(4-difluoromethylphenyl)-2,4-imidazolidinedione;
5-(dimethylamino)methylene-1-n-butyl-3-(2,3-diethylphenyl)-2,4-imidazolidinedione;
5-(dimethylamino)methylene-1-methyl-3-(3-ethoxy-4-chlorophenyl)-2,4-imidazolidinedione;
5-(dimethylamino)methylene-1-(4-ethoxyphenyl)-3-ethyl-2,4-imidazolidinedione;
5-(dimethylamino)methylene-1,3-diethyl-2,4-imidazolidinedione;
5-(dimethylamino)methylene-1,3-diphenyl-2,4-imidazolidinedione;
5-(dimethylamino)methylene-1-sec-butyl-3-(2-fluoro-3-nitrophenyl)-2,4-imidazolidinedione
5-(diethylamino)methylene-1-n-propyl-3-(3,4-dinitrophenyl)-2,4-dimidazolidinedione;
5-(dimethylamino)methylene-1-ethyl-3-(3-trifluoromethylphenyl)-2,4-imidazolidinedione;
5-(diethylamino)methylene-1-methyl-3-(2,6-dimethoxyphenyl)-2,4-imidazolidinedione;
5-(dimethylamino)methylene-3-isopropyl-1-(4-ethoxyphenyl)-2,4-imidazolidinedione; and
5-(diethylamino)methylene-1-methyl-3-(2,6-diethoxyphenyl)-2,4-imidazolidinedione.

The reaction of the 5-(dialkylamino)methylene-2,4-imidazolidinone with phosphorus oxychloride according to the novel process of this invention typically is carried out in an aprotic solvent such as N,N-dimethylformamide. Other aprotic solvents that can be employed include esters such as ethyl acetate, ethers such as diethyl ether and tetrahydrofuran, aromatics such as benzene and toluene, and related aprotic solvents. The reaction generally is carried out at a temperature of about 0° to about 150° C., ideally at about 30° to about 100° C., or simply at the reflux temperature of the reaction solution. An excessive amount of phosphorous oxychloride, for example from about 1 to about 100 molar excess, generally is employed to ensure complete conversion of the imidazolidinone to the corresponding chloro substituted 2,3-dihydro-2-oxo-1H-imidazole carboxaldehyde, and also to act as a co-solvent for the reaction. The reaction usually is complete within about 1 to 5 hours, and the chloro imidazole can be isolated by adding the reaction mixture to water and then extracting the product into an organic solvent such as diethyl ether or ethyl acetate. Removal of the organic solvent then provides the desired chloro substituted imidazole carboxaldehyde. These derivatives are useful as intermediates and also have herbicidal activity, and are provided by this invention as new compositions of matter.

The 5-chloro-4-carboxaldehyde imidazoles can be reacted with alkali metal salts of lower alkyl alcohols or lower alkyl thiols to provide the 4-carboxaldehyde imidazoles of this invention wherein $R^3$ in the above general formula is lower alkoxy or lower alkylthio. The lower alkyl alcohols and lower alkyl thiols typically are reacted with strong alkali metal bases such as sodium hydroxide, lithium hydride, potassium hydroxide and the like to provide the corresponding alkali metal salts of the alcohols or thiols. The alkali metal salts readily react with 5-chloro imidazole derivatives to displace the chloro group and produce the corresponding 5-lower alkoxy or 5-lower alkylthio imidazole carboxaldehydes of the invention. The formation of alkali metal salts of alcohols and thiols and the subsequent reaction thereof with the chloro imidazoles generally is carried out in situ in a suitable organic solvent such as dimethylsulfoxide, dimethylformamide, or if desired the respective alcohol or thiol can serve as the reaction solvent. The entire reaction sequence generally is complete within about 1 to 8 hours when carried out at a temperature of about $-20°$ to about 50° C. The product, a 5-alkoxy or 5-alkylthio imidazole, is readily isolated by simply pouring the reaction mixture into water and extracting the product into an organic solvent such as ethyl acetate or diethyl ether. Removal of the solvent by evaporation and purification by normal methods gives a compound of the invention.

The 5-amino imidazole carboxaldehydes of the invention, compounds defined by the above general formula wherein X is O and $R^3$ is $NR^4R^5$, are prepared by reaction of the 5-chloro imidazole carboxaldehydes with about a molar equivalent or slight excess of a secondary amine of the formula $R^4R^5NH$, for instance dimethylamine, diethylamine or the like. This reaction can be carried out in a suitable solvent such as water, and generally is complete after about 2 to about 10 hours when conducted at about 20° to about 80° C. Isolation of the product, a 5-amino-4-carboxaldehyde derivative, is readily accomplished by extraction of the reaction mixture into a suitable organic solvent such as benzene or ethyl acetate. Removal of the solvent by evaporation under reduced pressure provides the 5-amino-4-carboxaldehyde product of this invention, which can be further purified if desired by standard methods such as crystallization or chromatography.

All of the imidazole carboxaldehydes defined by the above formula wherein X is oxygen are potent herbicides, and also serve as intermediates in the synthesis of the imidazoles of this invention in which X in the above formula is N-lower alkyl. For example, compounds provided by this invention having the above general formula wherein X is N-lower alkyl are prepared by reaction of a lower alkyl primary amine with a compound of the above formula wherein X is O. The reaction follows the sequence:

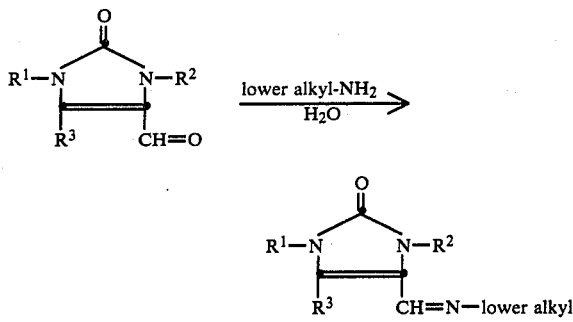

The reactants generally are employed in approximately equimolar quantities, and the reaction is best conducted in a suitable solvent such as water. When carried out at a temperature of about 20° to about 100° C., the reaction is typically complete in about 8 to about 48 hours. Isolation of the product can be accomplished by extraction into a water immiscible solvent such as diethyl ether. Evaporation of the solvent then provides the 4-(lower alkylimino)methylimidazole of this invention, which can be purified by crystallization or the like.

The preparation of specific compounds provided by this invention will be illustrated by the following detailed examples.

PREPARATION 1

The following preparation illustrates the synthesis of a 2,4-imidazolidinedione which is used as a starting material in the synthesis of the compounds of this invention.

A. To a stirred solution of 70 g. of N-methylaminoacetic acid in 500 ml. of water containing 70 g. of sodium hydroxide were added portion-wise over twenty minutes 100 g. of phenyl isocyanate. Following complete addition, the aqueous reaction mixture was stirred at 24° C. for two hours. The mixture was then filtered and the filtrate was acidified to pH 2 by the addition of conc. hydrochloric acid. The precipitate which formed was collected by filtration to provide N-methyl-N-hydroxycarbonylmethyl-N'-phenylurea.

B. The urea thus formed was dissolved in 250 ml. of deionized water containing 250 ml. of concentrated hydrochloric acid. The aqueous acidic reaction mixture was heated at reflux for three hours, and then poured onto 500 g. of ice. The precipitate which formed was collected by filtration and air dried to provide 35 g. of 1-methyl-3-phenyl-2,4-imidazolidinedione. M.P. 105°-106° C.

PREPARATION 2-11

Following the same general procedure, the imidazolidinediones listed below were prepared by reaction of an isocyanate with an N-substituted amino acetic acid derivtive:

1-methyl-3-(4-chlorophenyl)-2,4-imidazolidinedione; m.p. 117°-118° C.
1-methyl-3-(3-chlorophenyl)-2,4-imidazolidinedione; m.p. 78°-80° C.
1-methyl-3-(3-nitrophenyl)-2,4-imidazolidinedione; m.p. 142°-143° C.
1-methyl-3-(4-methylphenyl)-2,4-imidazolidinedione; m.p. 110°-111° C.
1-methyl-3-(4-methoxyphenyl)-2,4-imidazolidinedione; m.p. 112°-114° C.
1-methyl-3-(3-trifluoromethylphenyl)-2,4-imidazolidinedione; m.p. 87°-88° C.
1-methyl-3-(3-methylphenyl)-2,4-imidazolidinedione;
1-methyl-3-(2-chlorophenyl)-2,4-imidazolidinedione;
1-methyl-3-(3,4-dichlorophenyl)-2,4-imidazolidinedione; m.p. 135°-136° C.
1-methyl-3-cyclohexyl-2,4-imidazolidinedione;
Analysis calc. for $C_{10}H_{16}N_2O_6$: Theory: C, 61.20; H, 8.22; N, 14.27; Found: C, 61.42; H, 8.19; N, 14.05.

PREPARATION 12

The following demonstrates the preparation of 5-(dimethylamino)methylene-2,4-imidazolidinediones which can be employed as intermediates in the synthesis of the compounds provided by this invention.

A solution of 35 g. of 1-methyl-3-phenyl-2,4-imidazolidinedione in 200 ml. of N,N-dimethylformamide dimethylacetal was heated at reflux for twelve hours. The reaction mixture was cooled to room temperature, and the product crystallized as a white solid. The solid was collected by filtration and dried to give 24 g. of 5-(dimethylamino)methylene-1-methyl-3-phenyl-2,4-imidazolidinedione. M.P. 131°-133° C.

PREPARATIONS 13-23

The following 5-(dimethylamino)methylene-2,4-imidazolidinediones were prepared by reacting the appropriate 2,4-imidazolidinedione with the dimethylacetal of N,N-dimethylformamide according to the general procedure of Preparation 12 above.

5-(Dimethylamino)methylene-3-methyl-1-(3-trifluoromethylphenyl)-2,4-imidazolidinedione m.p. 103°-104° C.
5-(Dimethylamino)methylene-1-methyl-3-(3-methylphenyl)-2,4-imidazolidinedione m.p. 120°-121° C.
5-(Dimethylamino)methylene-1-methyl-3-(4-methylphenyl)-2,4-imidazolidinedione m.p. 162°-164° C.
5-(Dimethylamino)methylene-1-methyl-3-(2-chlorophenyl)-2,4-imidazolidinedione m.p. 149°-150° C.
5-(Dimethylamino)methylene-1-methyl-3-(3-chlorophenyl)-2,4-imidazolidinedione.
5-(Dimethylamino)methylene-1-methyl-3-(3,4-dichlorophenyl)-2,4-imidazolidinedione m.p. 132°-134° C.
5-(Dimethylamino)methylene-1-methyl-3-(3-nitrophenyl)-2,4-imidazolidinedione m.p. 179°-180° C.
5-(Dimethylamino)methylene-1-methyl-3-(4-chlorophenyl)-2,4-imidazolidinedione m.p. 171°-173° C.
5-(Dimethylamino)methylene-1-methyl-3-(3-trifluoromethylphenyl)-2,4-imidazolidinedione m.p. 132°-134° C.

5-(Dimethylamino)methylene-1-methyl-3-(4-methoxyphenyl)-2,4-imidazolidinedione m.p. 182°–184° C.

EXAMPLE 1

5-(Dimethylamino)-2,3-dihydro-3-methyl-2-oxo-1-phenyl-1H-imidazole-4-carboxaldehyde A mixture comprised of 75 ml. of phosphorus oxychloride, 5 ml of N,N-dimethylformamide, and 7.0 g. of the 5-(dimethylamino)methylene-1-methyl-3-phenyl-2,4-imidazolidinedione from Preparation 12 above was heated at reflux for two hours. The mixture was cooled to 30° C. and concentrated under reduced pressure to about one-half volume. The resulting mixture was poured over 200 g. of ice, and the resulting aqueous mixture was extracted several times with chloroform. The organic extracts were combined and the solvent was removed by evaporation under reduced pressure to give 4.7 g. of 5-chloro-3-methyl-1-phenyl-2,3-dihydro-2-oxo-1H-imidazole-4-carboxaldehyde. M.P. 182°–183° C.

To 4.5 g. of the 5-chloroimidazole derivative thus prepared was added 25 ml. of 25% aqueous dimethylamine. The solution was stirred for thirty minutes at 25° C., and then was diluted with 100 ml. of water. The aqueous reaction mixture was extracted several times with ethyl acetate. The organic extracts were combined, washed with fresh water, dried, and the solvent was removed by evaporation under reduced pressure to give 3.8 g. of 5-(dimethylamino)-2,3-dihydro-3-methyl-2-oxo-1-phenyl-1H-imidazole-4-carboxaldehyde. M.P. 160°–162° C.

Analysis calc. for $C_{13}H_{15}N_3O_2$: Theory: C, 63.66; H, 6.16; N, 17.13; Found: C, 63.45; H, 5.88; N, 16.87.

The following compounds of the present invention were prepared by the general procedure of Example 1.

EXAMPLE 2

1-(4-chlorophenyl)-5-(dimethylamino)-2,3-dihydro-3-methyl-2-oxo-1H-imidazole-4-carboxaldehyde. M.P. 172°–173° C.

Analysis calculated for $C_{13}H_{14}ClN_3O_2$: Theory: C, 55.82; H, 5.04; N, 15.02; Cl, 12.67; Found: C, 55.79; H, 4.94; N, 14.92; Cl, 12.85.

EXAMPLE 3

1-(3-Chlorophenyl)-5-(dimethylamino)-2,3-dihydro-3-methyl-2-oxo-1H-imidazole-4-carboxaldehyde. M.P. 99°–100° C.

Analysis calculated for $C_{13}H_{14}ClN_3O_2$: Theory: C, 55.82; H, 5.04; N, 15.02; Cl, 12.67; Found: C, 55.61; H, 4.82; N, 15.00; Cl. 12.93.

EXAMPLE 4

1-(4-Chlorophenyl)-5-(dimethylamino)-1,3-dihydro-3-methyl-4-[(methylimino)methyl]-2H-imidazol-2-one. M.P. 130°–131° C.

Analysis calculated for $C_{14}H_{17}ClN_4O$: Theory: C, 57.44; H, 5.85; N, 19.14; Cl, 12.11; Found: C, 57.65; H, 5.60; N, 19.38; Cl, 12.35.

EXAMPLE 5

1-(3-Nitrophenyl)-5-(dimethylamino)-2,3-dihydro-3-methyl-2-oxo-1H-imidazole-4-carboxaldehyde. M.P. 185°–186° C.

Analysis calculated for $C_{13}H_{14}N_4O_4$: Theory: C, 53.79; H, 4.86; N, 19.30; Found: C, 53.56; H, 4.75; N, 19.41.

EXAMPLE 6

(1-(4-Methylphenyl)-5-(dimethylamino)-2,3-dihydro-3-methyl-2-oxo-1H-imidazole-4-carboxaldehyde. M.P. 137°–139° C.

Analysis calculated for $C_{14}H_{17}N_3O_2$: Theory: C, 64.85; H, 6.61; N, 16.20; Found: C, 64.85; H, 6.41; N, 16.50.

EXAMPLE 7

1-(4-Methoxyphenyl)-5-(dimethylamino)-2,3-dihydro-3-methyl-2-oxo-1H-imidazole-4-carboxaldehyde. M.P. 135°–136° C.

Analysis calculated for $C_{14}H_{17}N_3O_3$: Theory: C, 61.08; H, 6.22; N, 15.26; Found: C, 61.32; H, 6.22; N, 15.36.

EXAMPLE 8

1-(4-Methylphenyl)-5-(dimethylamino)-1,3-dihydro-3-methyl-4-[(methylimino)methyl]-2H-imidazol-2-one. M.P. 134°–135° C.

Analysis calculated for $C_{15}H_{20}N_4O$: Theory: C, 66.15; H, 7.40; N, 20.57; Found: C, 66.19; H, 7.15; N, 20.62.

EXAMPLE 9

3-[3-(trifluoromethyl)phenyl]-5-(dimethylamino)-2,3-dihydro-1-methyl-2-oxo-1H-imidazole-4-carboxaldehyde. M.P. 127°–128° C.

Analysis calculated for $C_{14}H_{14}F_3N_3O_2$: Theory: C, 53.68; H, 4.50; N, 13.41; F, 18.19; Found: C, 53.87; H, 4.52; N, 13.17; F, 18.11.

EXAMPLE 10

1-(3-Methylphenyl)-5-(dimethylamino)-2,3-dihydro-3-methyl-2-oxo-1H-imidazole-4-carboxaldehyde. M.P. 95°–96° C.

Analysis calculated for $C_{14}H_{17}N_3O_2$: Theory: C, 64.85; H, 6.66; N, 16.20; Found: C, 64.79; H, 6.39; N, 16.23.

EXAMPLE 11

1-(3-Methylphenyl)-5-chloro-2,3-dihydro-3-methyl-2-oxo-1H-imidazole-4-carboxaldehyde. M.P. 143°–145° C.

Analysis calculated for $C_{12}H_{11}ClN_2O_2$: Theory: C, 57.50; H, 4.42; N, 11.17; Cl, 14.14; Found: C, 57.33; H, 4.25; N, 11.16; Cl, 14.21.

EXAMPLE 12

1-(3-Chlorophenyl)-5-chloro-2,3-dihydro-3-methyl-2-oxo-1H-imidazole-4-carboxaldehyde. M.P. 183°–184° C.

Analysis calculated for $C_{11}H_8Cl_2N_2O_2$: Theory: C, 48.73; H, 2.97; N, 10.33; Cl, 26.15; Found: C, 48.94; H, 3.07; N, 10.59; Cl, 26.37.

EXAMPLE 13

1-(4-Methylphenyl)-5-chloro-2,3-dihydro-3-methyl-2-oxo-1H-imidizole-4-carboxaldehyde. M.P. 218°–220° C.

Analysis calculated for $C_{12}H_{11}ClN_2O_2$: Theory: C, 57.50; H, 4.42; N, 11.17; Cl, 14.14; Found: C, 57.54; H, 4.33; N, 11.43; Cl, 14.06.

EXAMPLE 14

1-(3-Trifluoromethyl)phenyl-5-chloro-2,3-dihydro-3-methyl-2-oxo-1H-imidazole-4-carboxaldehyde Sarcosine (methylaminoacetic acid), 4.45 g., was dissolved in 15 ml. water containing 3.0 g. sodium hydroxide. The mixture was stirred rapidly while 9.36 g. of 3-(trifluoromethyl)phenylisocyanate was added dropwise. The reaction mixture was stirred for 10 minutes after the addition was complete. The product was collected by filtration, slurried in water and acidified with concentrated hydrochloric acid. The white solid was collected, dried and recrystallized from ethanol-water to provide 6.89 g. of N-(3-trifluoromethyl)phenylcarbonyl)sacrosine. M.P. 160°–162° C.

Analysis calculated for $C_{11}H_{11}F_3N_2O_3$: Theory: C, 47.83; H, 4.01; N, 10.14; F, 20.63; Found: C, 47.99; H, 4.00; N, 10.09; F, 20.61.

To 5.3 g. N-(3-(trifluoromethyl)phenylcarbonyl)sacrosine was added 50 ml. concentrated hydrochloric acid and the mixture was refluxed for 15 minutes. The mixture was cooled and diluted with 50 ml. water and 10 ml. ethanol to yield, following filtration and air drying, 4.82 g. of a white solid identified as 1-(3-(trifluoromethyl)phenyl)-2,3-dihydro-3-methyl-2,5-dioxo-2(1H)-imidazole. M.P. 74°–77° C.

A mixture of 4.74 g. of 1-(3-(trifluoromethyl)phenyl)-2,3-dihydro-3-methyl-2,5-dioxo-2(1H)-imidazole, 40 ml. phosphorus oxychloride and 5 ml. DMF was stirred at reflux for 2 hours and cooled. The volatiles were removed in vacuo and the residue was hydrolyzed with water. The pH was raised to 8 with concentrated NaOH and the water was removed in vacuo. The residue was dissolved in chloroform and the organic filtrate was evaporated. The resulting gum was chromatographed on silica gel using 40% EtOAc/hexane (v/v) as eluant. The appropriate fractions were combined and the solvent was removed to give a product that was recrystallized from cyclohexane to yield 750 mg. of 1-(3-trifluoromethyl)phenyl)-5-chloro-2,3-dihydro-3-methyl-2-oxo-1H-imidazole-4-carboxaldehyde. M.P. 130°–131° C.

EXAMPLE 15

1-(3-(Trifluoromethyl)phenyl-5-(dimethylamino)-2,3-dihydro-3-methyl-2-oxo-1H-imidazole-4-carboxaldehyde A solution of 750 mg. of 1-(3-(trifluoromethyl)phenyl)-5-chloro-2,3-dihydro-3-methyl-2-oxo-1H-imidazole-4-carboxaldehyde from Example 14 and 15 ml. of 25% aqueous dimethylamine was warmed on a steam bath for 5 minutes. The solution was cooled and the solid was collected by filtration and recrystallized from ethanol-water. After drying the product at 50° C. for 30 minutes, 320 mg. of 1-(3-trifluoromethyl)phenyl)-5-chloro-2,3-dihydro-3-methyl-2-oxo-1H-imidazole-4-carboxaldehyde was recovered. M.P. 87°–90° C.

Analysis calculated for $C_{14}H_{14}F_3N_2O_2$: Theory: C, 53.68; H, 4.50; N, 13.41; F, 18.19; Found: C, 53.42; H, 4.25; N, 13.34; F, 18.23.

The following compounds of the present invention were prepared by the general procedure of the immediately preceding Example.

EXAMPLE 16

1-(2-Chlorophenyl)-5-(dimethylamino)-2,3-dihydro-3-methyl-2-oxo-1H-imidazole-4-carboxaldehyde. M.P. 150°–152° C.

Analysis calculated for $C_{13}H_{14}ClN_3O_2$: Theory: C, 55.82; H, 5.04; N, 15.02; Cl, 12.67; Found: C, 55.59; H, 5.20; N, 14.96; Cl, 12.36.

EXAMPLE 17

1-(3,4-Dichlorophenyl)-5-dimethylamino-2,3-dihydro-3-methyl-2-oxo-1H-imidazole-4-carboxaldehyde. M.P. 186°–187° C.

Analysis calculated for $C_{13}H_{13}Cl_2N_3O_2$: Theory: C, 49.70; H, 4.17; N, 13.38; Cl, 22.57; Found: C, 49.53; H, 4.19; N, 13.11; Cl, 22.53.

EXAMPLE 18

1-(3,4-Dichlorophenyl)-5-(diethylamino)-2,3-dihydro-3-methyl-2-oxo-1H-imidazole-4-carboxaldehyde. M.P. 144°–145° C.

Analysis calculated for $C_{15}H_{17}Cl_2N_3O_2$: Theory: C, 52.65; H, 5.01; N, 12.28; Cl, 20.72; Found: C, 52.59; H, 5.16; N, 12.06; Cl, 20.96.

EXAMPLE 19

1-(3,4-Dichlorophenyl)-5-methoxy-2,3-dihydro-3-methyl-2-oxo-1H-imidazole-4-carboxaldehyde. M.P. 163°–164° C.

Analysis calculated for $C_{12}H_{10}Cl_2N_2O_3$: Theory: C, 47.84; H, 3.32; N, 9.30; Cl, 23.59; Found: C, 47.78; H, 3.55; N, 9.32; Cl, 23.82.

EXAMPLE 20

1-(3,4-Dichlorophenyl)-5-(methylthio)-2,3-dihydro-3-methyl-2-oxo-1H-imidazole-4-carboxaldehyde. M.P. 115°–117° C.

Analysis calculated for $C_{12}H_{10}Cl_2N_2O_2S$: Theory: C, 45.44; H, 3.18; N, 8.83; Found: C, 45.49; H, 3.15; N, 8.82.

EXAMPLE 21

1-(3,4-Dichlorophenyl)-5-[N-methyl-N-(2-propenyl)amino]-2,3-dihydro-3-methyl-2-oxo-1H-imidazole-4-carboxaldehyde. M.P. 107°–108° C.

Analysis calculated for $C_{15}H_{15}Cl_2N_3O_2$: Theory: C, 52.96; H, 4.44; N, 12.35; Found: C, 52.78; H, 4.24; N, 12.54.

EXAMPLE 22

1-Cyclohexyl-5-(dimethylamino)-2,3-dihydro-3-methyl-2-oxo-1H-imidazole-4-carboxaldehyde. M.P. 125°–126° C.

Analysis calculated for $C_{13}H_{21}N_3O_2$ Theory: C, 62.13; H, 8.42; N, 16.72; Found: C, 61.91; H, 8.66; N, 16.51.

EXAMPLE 23

1-(3,4-Dichlorophenyl)-5-chloro-1,3-dihydro-3-methyl-4-[(methylimino)methyl]-2H-imidazol-2-one.

To a stirred solution of 89 g. of sarcosine in 300 ml. of water containing 60 g. of sodium hydroxide were added portion-wise over thirty minutes 188 g. of 3,4-dichlorophenyl isocyanate. The reaction mixture was stirred for thirty minutes following the addition, and then was filtered. The filtrate was acidified with concentrated hydrochloric acid, whereupon a white solid precipitated. The solid was collected by filtration and air dried to give 1-methyl-1-(hydroxycarbonylmethyl)-3-(3,4-dichlorophenyl) urea. M.P. 103°–105° C.

Reaction of the urea thus formed with concentrated hydrochloric acid under reflux temperature for thirty minutes provided, following crystallization from ethyl acetate, 1-methyl-3-(3,4-dichlorophenyl)imidazolidine-2,4-dione. M.P. 135°–136° C.

A mixture of 8 g. of the imidazolidinedione thus prepared in 75 ml. of phosphorous oxychloride and 10 ml. of DMF was heated at reflux for one hour. The excessive phosphorous oxychloride was then removed from the reaction mixture by evaporation under reduced pressure. The reaction mixture was diluted with 50 ml. of water, and the product was extracted into ethyl acetate. Purification of the product over a silica gel/ethyl acetate column provided 3.2 g. of 1-(3,4-dichlorophenyl)-5-chloro-1,3-dihydro-3-methyl-2-oxo-1H-imidazole-4-carboxaldehyde. M.P. 195°–197° C.

A solution of 1.4 g. of the carboxaldehyde thus formed in 50 ml. of 40% aqueous methylamine was stirred at room temperature for forty-eight hours. The reaction mixture was then filtered to give a white solid that, when recrystallized from ethyl acetate, afforded 575 mg. of 1-(3,4-dichlorophenyl)-5-chloro-1,3-dihydro-3-methyl-4-[(methylimino)methyl]-2H-imidazol-2-one. M.P. 172°–174° C.

Analysis calculated for $C_{12}H_{10}Cl_3N_3O$: Theory: C, 45.21; H, 3.14; N, 13.19; Found: C, 45.35; H, 3.21; N, 13.08.

The following additional 5-chloroimidazole carboxaldehydes were synthesized by reaction of phosphorous oxychloride with a 5-(dimethylamino)methylene-1-methyl-3-substituted-2,4-imidazolidinedione in the presence of N,N-dimethylformamide.

EXAMPLE 24

1-(3-Nitrophenyl)-5-chloro-1,3-dihydro-3-methyl-2-oxo-1H-imidazole-4-carboxaldehyde. M.P. 188°–190° C. 40% yield.

EXAMPLE 25

1-(4-Chlorophenyl)-5-chloro-1,3-dihydro-3-methyl-2-oxo-1H-imidazole-4-carboxaldehyde. 73% yield.

EXAMPLE 26

1-(4-Methoxyphenyl)-5-chloro-1,3-dihydro-3-methyl-2-oxo-1H-imidazole-4-carboxaldehyde. M.P. 129°–130° C. 82% yield.

EXAMPLE 27

1-(2-Chlorophenyl)-5-chloro-1,3-dihydro-3-methyl-2-oxo-1H-imidazole-4-carboxaldehyde. M.P. 138°–141° C. 16% yield.

EXAMPLE 28

1-(Cyclohexyl)-5-chloro-1,3-dihydro-3-methyl-2-oxo-1H-imidazole-4-carboxaldehyde. M.P. 140°–142° C. 54% yield.

The imidazole carboxaldehyde derivatives provided by this invention have been found to display useful pre- and post-emergence herbicidal activity against a variety of weed species commonly occurring in areas utilized for growing desired crops such as the cereal grains, corn, soybeans and the like. The selective herbicidal activity of the compounds has been analyzed in a number of standard greenhouse tests. One such test was a broad spectrum greenhouse test carried out by filling square plastic pots with a sterilized sandy loam soil and planting seeds of tomato, large crabgrass and pigweed. Each pot was fertilized with a 23-21-17 fertilizer four days before treatment with test compound.

The test compounds were formulated for application by dissolving each compound in a solution comprising 100 ml. of acetone and 100 ml. of ethanol plus 1.174 g. of Tomixul R and 0.783 g. of Toximul S. (Toximul R and Toximul S are proprietary blends of anionic and nonionic surfactants manufactured by Stephan Chemical Company, Northfield, IL. Each test compound was dissolved in the diluent at the rate of 20 mg. per 2 ml. of solvent, and then the solution was diluted to 8 ml. with deionized water. The formulated compounds were applied to the planted pots at an effective rate of 15 pounds per acre (16.816 kilograms per hectare).

Test compounds were applied postemergence to some planted pots and preemergence to others. The postemergence applications were made by spraying the solution containing the test compound over the emerged plants about twelve days after the seeds were planted. Preemergence applications were sprayed on the soil one day after the seeds were planted.

Following application of the test compounds, the pots were placed in a greenhouse and watered as necessary. Observations were conducted about 10–13 days following application of the test compounds, and untreated control plants were used as standards in each observation. The degree of herbicidal activity of the test compounds was determined by rating the treated plants on a scale of 1–5. On this scale, "1" indicates no plant injury; "2" is slight injury; "3" is moderate plant injury: "4" is severe injury and "5" is death of the plant or no seedling emergence. The type of plant injury sustained by the plants was tabulated using the following code letters:

A = abscission of leaves
B = burned
C = chlorsis
D = death
E = epinasty
S = stunting Table I below presents the herbicidal activity of representative compounds of the invention when evaluated according to the foregoing method.

TABLE 1

| Compound of Example No. | Preemergence | | | Postemergence | | |
|---|---|---|---|---|---|---|
| | Toma-to | Large Crab-grass | Pig-weed | Toma-to | Large Crab-grass | Pig-weed |
| 1 | 4BS | 3BS | 4BS | 5D | 4BS | 5D |
| 2 | 3BS | 3BS | 4BS | 5D | 5D | 5D |
| 3 | 3BS | 3BS | 3BS | 5D | 5D | 5D |
| 4 | 3S | 3S | 4BS | 5D | 4BS | 5D |
| 5 | 1 | 2S | 1 | 2BS | 1 | 2C |
| 6 | 2S | 2S | 3BS | 5D | 3BS | 4BS |
| 7 | 2S | 3S | 4BS | 5D | 3BS | 5D |
| 8 | 3S | 3S | 3S | 4BS | 2BS | 4BS |
| 9 | 3BS | 3BS | 2BS | 4BS | 3BS | 3BS |
| 10 | 3BS | 3BS | 3BS | 4BS | 5D | 5D |
| 11 | 3BS | 4BS | 4BS | 5D | 4BS | 5D |
| 12 | 2S | 2S | 2S | 1 | 1 | 2B |
| 13 | 1 | 3S | 2S | 1 | 1 | 1 |
| 16 | 5N | 2BS | 2S | 2B | 1 | 2B |
| 22 | 1 | 2S | 3S | 4BS | 1 | 3BS |

A similar greenhouse study utilizing seven seed species was carried out to further evaluate preemergence and postemergence herbicidal activity of the imidazole carboxaldehyde derivatives of this invention. The compounds to be evaluated were formulated according to the procedure outlined above, except that about 4 g/100 ml of the compound were dissolved in the surfactant-containing solvent, and about 1 part of the organic solution was diluted with 12 parts of water before application to seeded containers. The compounds were applied at the effective rate of 8 lbs/acre (8.96 kg/ha). Typical results of such evaluation are presented in Table II below. Certain of the compounds were also applied postemergence at concentrations less than 8 lbs/acre. These results are presented in Table III below.

TABLE II

| Compound of Example Number | Preemergence | | | | | | | Postemergence | | | | | | |
|---|---|---|---|---|---|---|---|---|---|---|---|---|---|---|
| | Corn | Large Crab-grass | Pig-weed | Foxtail | Velvet Leaf | Morning-glory | Zinnia | Corn | Large Crab-grass | Pig-weed | Foxtail | Velvet Leaf | Morning-glory | Zinnia |
| 1 | 2 | 4 | 5 | 3 | 5 | 3 | 3 | 1 | 1 | 4 | 3 | 3 | 3 | 3 |
| 2 | 3 | 5 | 5 | 5 | 5 | 4 | 4 | 3 | 2 | 4 | 4 | 5 | 4 | 3 |
| 3 | 3 | 4 | 5 | 5 | 4 | 4 | 5 | 3 | 3 | 5 | 4 | 4 | 4 | 4 |
| 4 | 4 | 5 | 5 | 5 | 5 | 3 | 5 | 2 | 3 | 4 | 3 | 3 | 3 | 3 |
| 5 | 1 | 2 | 1 | 1 | 2 | 1 | 1 | 1 | 1 | 1 | 1 | 1 | 2 | 1 |
| 6 | 1 | 3 | 3 | 1 | 3 | 2 | 2 | 2 | 2 | 2 | 2 | 3 | 3 | 3 |
| 7 | 1 | 3 | 2 | 2 | 2 | 3 | 2 | 2 | 2 | 2 | 2 | 2 | 3 | 3 |
| 8 | 1 | 3 | 3 | 2 | 5 | 2 | 3 | 2 | 1 | 2 | 1 | 2 | 3 | 3 |
| 9 | 1 | 2 | 2 | 1 | 1 | 1 | 2 | 1 | 1 | 1 | 2 | 1 | 1 | 2 |
| 10 | 2 | 5 | 4 | 4 | 5 | 4 | 4 | 2 | 2 | 4 | 2 | 3 | 3 | 3 |
| 11 | 1 | 3 | 4 | 2 | 3 | 2 | 2 | 1 | 1 | 1 | 1 | 1 | 1 | 1 |
| 12 | 1 | 4 | 5 | 3 | 3 | 2 | 3 | 1 | 1 | 1 | 1 | 1 | 1 | 1 |
| 13 | 1 | 2 | 3 | 1 | 2 | 2 | 2 | 1 | 1 | 1 | 1 | 1 | 1 | 1 |
| 14 | 1 | 3 | 4 | 3 | 2 | 4 | 3 | 1 | 1 | 1 | 1 | 1 | 1 | 1 |
| 15 | 2 | 5 | 5 | 4 | 4 | 4 | 5 | 2 | 3 | 4 | 4 | 4 | 3 | 3 |
| 16 | 1 | 3 | 5 | 2 | 4 | 1 | 2 | 1 | 1 | 1 | 1 | 2 | 2 | 2 |
| 17 | 2 | 5 | 5 | 5 | 5 | 5 | 5 | 1 | 2 | 3 | 2 | 2 | 3 | 2 |
| 18 | 1 | 4 | 5 | 4 | 4 | 3 | 5 | 3 | 4 | 5 | 4 | 3 | 3 | 4 |
| 19 | 1 | 4 | 4 | 2 | 3 | 1 | 2 | 1 | 2 | 3 | 2 | 1 | 1 | 2 |
| 20 | 1 | 4 | 5 | 4 | 3 | 1 | 1 | 1 | 2 | 2 | 3 | 1 | 1 | 1 |
| 21 | 1 | 4 | 5 | 4 | 3 | 2 | 3 | 2 | 4 | 4 | 3 | 3 | 4 | 3 |
| 22 | 1 | 3 | 5 | 3 | 3 | 1 | 2 | 1 | 1 | 2 | 1 | 1 | 1 | 2 |
| 23 | 1 | 4 | 5 | 4 | 4 | 1 | 1 | 1 | 1 | 1 | 1 | 1 | 1 | 1 |

TABLE III

| Compound of Example No. | Rate of Application lbs/acre (kg/ha) | Postemergence | | | | | | |
|---|---|---|---|---|---|---|---|---|
| | | Corn | Large Crabgrass | Pigweed | Foxtail | Velvet Leaf | Morningglory | Zinnia |
| 2 | 4 (4.48) | 1 | 2 | 4 | 2 | 4 | 3 | 3 |
| | 2 (2.24) | 1 | 2 | 2 | 2 | 3 | 2 | 2 |
| | 1 (1.12) | 1 | 2 | 2 | 2 | 2 | 2 | 2 |
| 3 | 4 (4.48) | 1 | 2 | 3 | 2 | 3 | 3 | 3 |
| | 2 (2.24) | 1 | 2 | 3 | 2 | 2 | 2 | 3 |
| | 1 (1.12) | 1 | 1 | 2 | 1 | 1 | 2 | 2 |
| 15 | 4 (4.48) | 1 | 3 | 3 | 3 | 3 | 2 | 3 |
| | 2 (2.24) | 1 | 2 | 2 | 3 | 1 | 2 | 2 |
| | 1 (1.12) | 1 | 2 | 1 | 2 | 1 | 1 | 2 |
| 18 | 4 (4.48) | 1 | 1 | 2 | 1 | 1 | 2 | 2 |
| | 2 (2.24) | 1 | 1 | 1 | 1 | 1 | 1 | 1 |
| | 1 (1.12) | 1 | 1 | 1 | 1 | 1 | 1 | 1 |
| 21 | 4 (4.48) | 1 | 3 | 3 | 3 | 2 | 3 | 4 |
| | 2 (2.24) | 1 | 3 | 3 | 2 | 1 | 3 | 3 |
| | 1 (1.12) | 1 | 3 | 3 | 2 | 1 | 2 | 3 |

The herbicidal activity of a number of the compounds of the invention was evaluated at various application rates in a multiple-species greenhouse test. Several additional weed and crop species were utilized to determine the herbicidal selectivity of the compounds. The compounds were formulated as described above, and applied preemergence to seeded flats. The results for several compounds of the invention are presented below in Table IV.

TABLE IV

| Compound of Example No. | Rate of Application Lbs/Acre (kg/ha) | Corn | Cotton | Soybean | Wheat | Alfalfa | Sugar Beet | Rice | Cucumber | Tomato | Barn-yard Grass | Lambs-quarter | Large Crab-grass | Mustard | Pigweed | Foxtail | Wildoat | Vel-vet-leaf | Jimson Weed | Morning-glory | Zinnia |
|---|---|---|---|---|---|---|---|---|---|---|---|---|---|---|---|---|---|---|---|---|---|
| 1 | 4 (4.48) | 3 | 2 | 5 | 3 | 1 | 4 | 2 | 4 | 4 | 3 | 5 | 5 | 4 | 5 | 4 | 3 | 5 | 5 | 4 | 4 |
|   | 2 (2.24) | 3 | 1 | 1 | 3 | 2 | 4 | 3 | 3 | 3 | 3 | 5 | 4 | 3 | 5 | 4 | 3 | 5 | 4 | 4 | 3 |
|   | 1 (1.12) | 1 | 1 | 1 | 1 | 2 | 4 | 3 | 2 | 1 | 2 | 5 | 5 | 4 | 4 | 4 | 3 | 5 | 5 | 4 | 4 |
|   | 0.5 (0.56) | 1 | 1 | 2 | 1 | 1 | 1 | 2 | 2 | 1 | 1 | 1 | 1 | 1 | 3 | 2 | 1 | 1 | 3 | 2 | 1 |
| 2 | 4 (4.48) | 1 | 1 | 1 | 1 | 1 | 4 | 2 | 4 | 4 | 3 | 5 | 4 | 3 | 5 | 4 | 3 | 4 | 3 | 1 | 2 |
|   | 2 (2.24) | 1 | 1 | 2 | 1 | 1 | 2 | 2 | 2 | 2 | 2 | 4 | 3 | 3 | 3 | 3 | 1 | 5 | 2 | 2 | 1 |
|   | 1 (1.12) | 1 | 1 | 1 | 1 | 1 | 3 | 2 | 2 | 1 | 2 | 5 | 3 | 3 | 5 | 4 | 1 | 2 | 2 | 1 | 2 |
| 3 | 4 (4.48) | 2 | 1 | 1 | 1 | 2 | 3 | 2 | 3 | 2 | 2 | 5 | 3 | 3 | 5 | 4 | 4 | 4 | 2 | 3 | 4 |
|   | 2 (2.24) | 1 | 1 | 1 | 1 | 1 | 3 | 1 | 2 | 2 | 2 | 3 | 3 | 4 | 4 | 3 | 1 | 4 | 3 | 3 | 3 |
|   | 1 (1.12) | 1 | 1 | 1 | 1 | 2 | 3 | 1 | 2 | 1 | 2 | 3 | 3 | 3 | 3 | 3 | 1 | 3 | 1 | 2 | 3 |
| 4 | 4 (4.48) | 1 | 1 | 1 | 1 | 1 | 1 | 1 | 1 | 4 | 2 | 3 | 2 | 3 | 4 | 2 | 1 | 4 | 3 | 2 | 2 |
|   | 2 (2.24) | 1 | 1 | 1 | 1 | 1 | 3 | 1 | 2 | 2 | 3 | 3 | 2 | 2 | 3 | 3 | 2 | 3 | 1 | 2 | 2 |
|   | 1 (1.12) | 1 | 1 | 1 | 1 | 1 | 2 | 1 | 1 | 1 | 1 | 2 | 1 | 1 | 1 | 1 | 1 | 2 | 1 | 1 | 2 |
| 8 | 4 (4.48) | 1 | 1 | 1 | 1 | 1 | 3 | 2 | 2 | 2 | 3 | 4 | 3 | 3 | 3 | 3 | 2 | 2 | 2 | 1 | 2 |
|   | 2 (2.24) | 1 | 1 | 1 | 1 | 1 | 1 | 1 | 1 | 1 | 1 | 2 | 2 | 1 | 1 | 2 | 1 | 2 | 1 | 1 | 2 |
|   | 1 (1.12) | 1 | 1 | 1 | 1 | 1 | 1 | 1 | 2 | 2 | 1 | 2 | 2 | 2 | 3 | 3 | 1 | 2 | 2 | 1 | 2 |
| 10 | 4 (4.48) | 1 | 1 | 1 | 1 | 3 | 3 | 2 | 4 | 4 | 2 | 4 | 4 | 3 | 3 | 3 | 1 | 3 | 3 | 3 | 3 |
|    | 2 (2.24) | 1 | 1 | 2 | 2 | 3 | 2 | 2 | 3 | 3 | 3 | 4 | 3 | 3 | 3 | 3 | 2 | 3 | 2 | 2 | 2 |
| 12 | 4 (4.48) | 1 | 1 | 2 | 1 | 1 | 3 | 2 | 2 | 1 | 2 | 2 | 2 | 1 | 2 | 2 | 1 | 2 | 1 | 1 | 1 |
|    | 2 (2.24) | 2 | 1 | 1 | 1 | 1 | 2 | 1 | 1 | 1 | 2 | 2 | 2 | 1 | 2 | 3 | 1 | 1 | 2 | 1 | 2 |
|    | 1 (1.12) | 1 | 1 | 1 | 1 | 1 | 1 | 1 | 1 | 1 | 1 | 1 | 1 | 1 | 1 | 1 | 1 | 1 | 1 | 1 | 1 |
| 14 | 4 (4.48) | 1 | 1 | 1 | 2 | 2 | 2 | 2 | 2 | 2 | 3 | 3 | 4 | 3 | 3 | 3 | 1 | 2 | 3 | 3 | 2 |
|    | 2 (2.24) | 1 | 1 | 1 | 1 | 1 | 2 | 2 | 2 | 2 | 2 | 2 | 3 | 2 | 2 | 3 | 1 | 1 | 2 | 1 | 1 |
| 15 | 4 (4.48) | 1 | 1 | 1 | 2 | 1 | 2 | 1 | 4 | 4 | 2 | 4 | 4 | 2 | 3 | 3 | 1 | 3 | 3 | 3 | 3 |
|    | 2 (2.24) | 1 | 1 | 1 | 1 | 1 | 3 | 2 | 2 | 2 | 2 | 2 | 3 | 2 | 2 | 3 | 1 | 2 | 1 | 1 | 2 |
| 16 | 4 (4.48) | 2 | 1 | 1 | 1 | 1 | 3 | 2 | 2 | 2 | 2 | 2 | 2 | 2 | 2 | 2 | 1 | 1 | 1 | 1 | 1 |
|    | 2 (2.24) | 2 | 1 | 1 | 1 | 1 | 1 | 1 | 1 | 1 | 1 | 1 | 1 | 1 | 1 | 2 | 1 | 1 | 1 | 1 | 1 |
|    | 1 (1.12) | 2 | 1 | 1 | 1 | 1 | 1 | 1 | 2 | 2 | 2 | 2 | 2 | 2 | 2 | 2 | 1 | 3 | 1 | 1 | 1 |
| 17 | 4 (4.48) | 1 | 1 | 1 | 2 | 4 | 4 | 2 | 5 | 4 | 5 | 5 | 5 | 4 | 4 | 4 | 4 | 5 | 3 | 2 | 5 |
|    | 2 (2.24) | 1 | 1 | 1 | 1 | 2 | 3 | 1 | 3 | 1 | 3 | 3 | 4 | 3 | 4 | 3 | 1 | 2 | 2 | 2 | 3 |
|    | 1 (1.12) | 1 | 1 | 1 | 1 | 1 | 2 | 2 | 2 | 1 | 3 | 3 | 3 | 2 | 3 | 2 | 1 | 2 | 1 | 1 | 1 |
| 18 | 4 (4.48) | 1 | 1 | 1 | 1 | 2 | 4 | 2 | 2 | 2 | 2 | 2 | 4 | 3 | 3 | 4 | 1 | 2 | 2 | 1 | 2 |
|    | 2 (2.24) | 1 | 1 | 1 | 1 | 1 | 2 | 1 | 1 | 1 | 1 | 1 | 4 | 2 | 2 | 2 | 1 | 2 | 2 | 1 | 1 |
|    | 1 (1.12) | 1 | 1 | 1 | 1 | 1 | 1 | 2 | 2 | 2 | 2 | 1 | 4 | 2 | 2 | 3 | 1 | 2 | 2 | 1 | 1 |
| 19 | 4 (4.48) | 1 | 2 | 1 | 1 | 1 | 3 | 2 | 2 | 2 | 2 | 3 | 4 | 3 | 5 | 4 | 1 | 3 | 2 | 3 | 2 |
|    | 2 (2.24) | 1 | 1 | 1 | 1 | 1 | 1 | 3 | 2 | 1 | 1 | 2 | 3 | 3 | 3 | 3 | 1 | 2 | 2 | 1 | 1 |
|    | 1 (1.12) | 1 | 1 | 1 | 1 | 1 | 1 | 1 | 1 | 1 | 1 | 1 | 3 | 1 | 1 | 1 | 1 | 1 | 1 | 1 | 1 |
| 22 | 4 (4.48) | 1 | 1 | 1 | 1 | 2 | 3 | 2 | 2 | 2 | 2 | 2 | 4 | 2 | 4 | 3 | 1 | 2 | 2 | 2 | 1 |
|    | 2 (2.24) | 1 | 1 | 1 | 1 | 1 | 2 | 2 | 2 | 1 | 1 | 1 | 3 | 1 | 3 | 2 | 1 | 4 | 2 | 2 | 1 |
|    | 1 (1.12) | 1 | 1 | 1 | 1 | 1 | 1 | 1 | 1 | 1 | 1 | 1 | 4 | 1 | 2 | 2 | 1 | 3 | 2 | 2 | 1 |
| 23 | 4 (4.48) | 1 | 1 | 1 | 1 | 2 | 5 | 2 | 2 | 2 | 2 | 2 | 4 | 3 | 3 | 4 | 1 | 5 | 3 | 1 | 1 |
|    | 2 (2.24) | 1 | 1 | 1 | 1 | 1 | 4 | 2 | 2 | 2 | 1 | 1 | 4 | 2 | 2 | 1 | 1 | 3 | 2 | 1 | 1 |
|    | 1 (1.12) | 1 | 1 | 1 | 1 | 1 | 1 | 1 | 1 | 1 | 1 | 1 | 4 | 1 | 1 | 1 | 1 | 1 | 1 | 1 | 1 |

The novel imidazole carboxaldehyde derivatives of this invention also have demonstrated activity against various strains of viral infection, including coxsachie, Mengo, A-21, vaccinia and polio virus. The compounds have shown marginal to good antifungal activity, and also have demonstrated good plant growth regulator activity.

As the data presented in the above Tables indicate, the imidazole carboxaldehyde derivatives provided by this invention possess useful selective herbicidal activity and therefore are of particular value in the control and elimination of undesired vegetative growth. One embodiment of this invention is a method for controlling undesired plant growth which comprises applying to plants whose growth is to be controlled or to the soil where such undesired plants are growing a herbicidally effective amount of a compound defined herein by the above general formula. A "herbicidally effective amount" as used herein will generally be an amount from about 0.1 to about 15.0 pounds of herbicidal agent per acre of soil (about 0.1 to about 16.8 kg/ha). The compounds are more preferably applied at rates of about 0.5 to about 10.0 pounds per acre (about 0.56 to about 11.2 kg/ha). The compounds are effective in controlling undesired vegetative growth when applied directly to the plant, for instance to the foliage when the plants are young, but are preferably employed by application to the soil prior to plant emergence, for instance to the locus where vegetative control is desired. If desired, the compounds can be incorporated into the soil, for instance by use of a conventional double disc or harrow prior to seeding to desired plants such as corn, soybeans, wheat and the like. It is preferred, however, that the compound simply be applied without incorporation to the soil before plant emergence, and that the compounds be permitted to leach into the soil with the assistance of natural rainfall. While the compounds are thus effective in the control of a wide variety of broadleaf and grassy weeds, a preferred practice of the invention is in the control of weeds such as pigweed, foxtail, velvet leaf, and morning-glory.

In still another embodiment of the invention there is provided a herbicidal composition comprising an imidazole carboxaldehyde derivative of the above formula together with an agronomically acceptable excipient, carrier or diluent. Such compositions generally will contain from about 0.1 to about 95.0 percent by weight of active imidazole ingredient. The particular amount of imidizole will of course be determined by the specific type of composition desired. Sprayable formulations are preferred, because of the rapidity and economy of application, and because sprayed applications do not drift to untreated areas as much as dusts do. Granular formulations may be used when the compounds are to be applied to the soil.

The inert portions of agricultural chemical formulations and the methods of manufacture of them are well known and conventional in the agricultural chemicals art. Only a brief explanation of such formulations containing the compounds of this invention will therefore be given.

Dusts formulations provided herein usually will contain from about 0.1 to about 5 percent by weight of an imidazole carboxaldehyde derivative. Dusts are prepared by intimately mixing and finely grinding the active compound with an agronomically acceptable carrier such as ground montmorillonite clay, attapulgus clay, talc, ground volcanic rock, kaolin clay, or other inert, relatively dense, inexpensive substance.

The most convenient formulations are in the form of cncentrated compositions to be applied by spraying as water dispersions or emulsions containing in the range from about 0.01 percent to about 5 percent of the active compound. Water-dispersible or emulsifiable compositions may be either solids, usually known as wettable powders, or liquids usually known as emulsifiable concentrates or aqueous suspensions.

A typical wettable powder comprises an intimate mixture of a compound of the invention, an inert agronomically acceptable carrier, and surfactants. The concentration of the active compound is usually from about 5 percent to about 90 percent by weight. The inert carrier is usually chosen from among the attapulgite clays, the montmorillonite clays, the diatomaceous earths, or the purified silicates. Effective surfactants, comprising from about 0.5 percent to about 10 percent by weight of the wettable powder, are chosen from among the sulfonated lignins, the condensed napthalenesulfonates, the napthalenesulfonates, the alkylbenzenesulfonates, the alkyl sulfates, and the nonionic surfactants such as ethylene oxide adducts of phenol.

A typical emulsifiable concentrate comprises from about 0.1 to about 4 lbs. of a compound of the invention per gallon of liquid, dissolved in a mixture of organic solvents and emulsifiers. The organic solvent is chosen with regard to its solvency and its cost. Useful solvents include the aromatics, especially the xylenes, and the hydrophilic solvents such as the higher alcohols, glycols such as ethylene glycol, and the hydroxy ethers such as 2-ethoxyethanol. Other organic solvents may also be used, including the terpenic solvents such as rosin and turpentine derivatives. Suitable emulsifiers for emulsifiable concentrates are chosen from the same types used for wettable powders, and are used at similar weight percentages.

Solid, granular compositions are convenient for the application of compounds of this invention to the soil. Granules comprise a compound of the invention dispersed on a granular inert agronomic carrier such as coarsely ground clay of from about 0.1 to about 3 mm. particle size. The compound is most conveniently applied to the clay by dissolving it in an inexpensive solvent and applying the solution to the sized clay in an appropriate solids mixer.

The formulated compounds of the invention are applied to plants in the manners conventional in agricultural chemistry. Sprayable compositions are easily applied by any of many types of sprayers available to the art. Self-propelled, tractor-mounted, and towed spray devices which apply the water-dispersed formulations through calibrated atomizing nozzles are available and effective. Metering applicators are also available which can apply accurately measured quantities of granular compositions to the soil. The operator of the application equipment need only take care to adjust the equipment to apply an amount of the water-dispersed or granular formulation per acre which supplies the desired application rate of the herbicidal compound, and to apply the amount uniformly to the plants to be treated.

The compositions provided herein can additionally contain other herbicides, for instance a urea such as linuron, a dinitroaniline such as trifluralin, a triazine such as metribuzin, an aniline such metalachlor or alachlor, and similar well known herbicides. Such compositions will generally take the form of a tank mix or the like.

The following examples provide an illustration of typical herbicidal compositions comprehended by this invention.

EXAMPLE 29

Wettable Powder

| Ingredient | Concentration by Weight (%) |
| --- | --- |
| 1-(3-Methylphenyl)-5-(dimethylamino)-2,3-dihydro-3-methyl-2-oxo-1H-imidazole-4-carboxaldehyde | 50 |
| Igepal CA = 6.30, a polyoxyethylene octyl phenol nonionic wetting agent-GAF Corp. | 20 |
| Bardens Clay | 30 |

The imidazole carboxaldehyde herbicide is finely divided into a powder and blended to uniformly with the agronomic carriers to form a free flowing powder that will be wetted and suspendible in water at or near the site of application to form a sprayable mixture. The composition is then sprayed on the locus where vegetative control is desired. The application is done at a volume rate so that the active ingredient is present at about 1 to about 4 pounds per acre (about 1.12 to about 4.48 kg/ha).

EXAMPLE 30

Dust

| Ingredient | Weight % |
| --- | --- |
| 1-(3,4-Dichlorophenyl)-5-(diethylamino)-2,3-dihydro-3-methyl-2-oxo-1H-imidazole-4-carboxaldehyde | 5 |
| Diatomite, a diatomaceous earth, Witco Chemical Corp., Inorganic Specialities Division | 95 |

The imidazole carboxaldehyde is suspended in acetone and sprayed onto the diatomaceous earth carrier. The solvent is then removed by evaporation and the dry mixture is ground to a fine powder of uniform particle size of about 10 to about 40 microns. The dust formulation can be diluted at the site of application if desired by the addition of additional excipient such as silica or clay. The dust is surface applied to the soil or plants where vegetative control is desired, either by conventional ground equipmet or aireally.

EXAMPLE 31

Tank Mix

| Ingredient | Weight % |
| --- | --- |
| 1-(3,4-Dichlorophenyl)-5-(methylthio)-2,3-dihydro-3-methyl-2-oxo-1H-imidazole-4-carboxaldehyde | 60 |
| N,N-di-n-propyl-2,6-dinitro-3-amino-4-trifluoromethylaniline (prodiamine) | 40 |

A wettable powder formulation containing 50% by weight of the imidazole carboxaldehyde is added to an agitated aqueous suspension of an emulsifiable concentrate formulation containing 25% by weight of the dinitroaniline herbicide. The mixture is agitated and sprayed onto the soil surface at the rate of about 3 pounds per acre (3.36 kg/ha) of imidazole carboxaldehyde and about 2 pounds per acre (2.24 kg/ha) of the dinitroaniline. The soil can then be seeded to soybeans or the like, and the crop is grown substantially free of unwanted vegetation such as crabgrass, fall panicum, purslane and the like.

EXAMPLE 32

Aqueous Suspension

| Ingredient | Weight % |
| --- | --- |
| 1-(3,4-Dichlorophenyl)-5-chloro-1,3-dihydro-3-methyl-4-[(methylimino)-methyl]-2H-imidazole-2-one | 60.0 |
| Reax, lignosulfonate suspending agent, Westvaco Corp., Polychemical Dept. | 5.0 |
| Zanthum Gum thickening agent | 0.15 |
| Zeosyl 100, a precipitated hydrated silicon dioxide anticaking agent | 1.0 |
| Antifoam C foam suppressant | 0.25 |
| Water | 33.60 |
| | 100.00 |

The aqueous suspension containing 60% by weight of the imidazole carboxaldehyde derivative is diluted with additional water at the site of application, and the mixture is sprayed onto the soil surface where vegetative control is desired at a rate so that the active ingredient contacts the soil at about 4 pounds per acre (4.48 kg/ha). If desired the soil can be agitated following the application, for instance by discing or harrowing.

We claim:

1. A compound of the formula

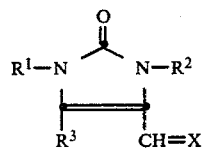

wherein:

$R^1$ and $R^2$ independently are lower alkyl, cycloalkyl, phenyl, or phenyl substituted with one or two groups selected from halo, lower alkyl, lower alkoxy, halo lower alkyl, or nitro;

$R^3$ is chloro, lower alkoxy, lower alkylthio or $NR^4R^5$, in which $R^4$ is methyl or ethyl and $R^5$ is methyl, ethyl or propenyl; and X is O or N-lower alkyl.

2. The compound of claim 1 wherein X is O or N—CH$_3$.

3. The compound of claim 2 wherein $R^2$ is methyl and $R^1$ is phenyl or mono-substituted phenyl.

4. The compound of claim 3 wherein $R^3$ is chloro.

5. The compound of claim 3 wherein $R^3$ is lower alkoxy or lower alkylthio.

6. The compound of claim 3 wherein $R^3$ is $NR^4R^5$.

7. The compound of claim 6 wherein $R^4$ is methyl and $R^5$ is methyl, ethyl or 2-propenyl.

8. The compound of claim 6 wherein $R^4$ is ethyl and $R^5$ is methyl, ethyl or 2-propenyl.

9. The compound of claim 6 wherein $R^1$ is phenyl, 3-chlorophenyl, 4-chlorophenyl, 3-methylphenyl, 4-methylphenyl, 3-nitrophenyl, 4-methoxyphenyl or 3-trifluoromethylphenyl.

10. The compound of claim 9 wherein $R^3$ is $NR^4R^5$ and X is O.

11. The compound of claim 10 wherein $R^3$ is $N(CH_3)_2$.

12. The compound of claim 2 wherein $R^1$ is phenyl, 3-chlorophenyl, 4-chlorophenyl, 3-methylphenyl, 4-methylphenyl, 3-nitrophenyl, 4-methoxyphenyl or 3-trifluoromethylphenyl.

13. The compound of claim 12 wherein $R^3$ is chloro.

14. The compound of claim 12 wherein $R^3$ is lower alkoxy or lower alkylthio.

15. A herbicidal method for controlling undesired plant growth comprising applying to said undesired plants or the the soil where vegetative control is desired a herbicidally effective amount of a compound of claim 1.

16. The method of claim 15 employing a compound wherein $R^1$ is phenyl, mono- or disubstituted phenyl and $R^2$ is lower alkyl.

17. The method of claim 16 employing a compound wherein $R^3$ is dimethylamino.

18. The method of claim 15 employing a compound wherein $R^1$ is lower alkyl and $R^2$ is phenyl, mono- or disubstituted phenyl.

19. The method of claim 18 employing a compound wherein $R^3$ is dimethylamino.

20. The method of claim 18 employing a compound wherein $R^1$ is methyl.

21. The method of claim 16 employing a compound wherein $R^1$ is phenyl, chlorophenyl, methylphenyl, methoxyphenyl, nitrophenyl, or trifluoromethylphenyl.

22. The method of claim 21 employing a compound wherein $R^1$ is phenyl, 3-chlorophenyl, 4-chlorophenyl, 3-methylphenyl, 4-methylphenyl, 3-nitrophenyl, 4-methoxyphenyl or 3-trifluoromethylphenyl.

23. The method of claim 15 employing a compound wherein X is O or N—$CH_3$.

24. A herbicidal composition comprising from about 0.1 to about 95.0 percent by weight of a compound of claim 1 admixed with an agronomically acceptable carrier.

25. The composition of claim 24 employing a compound wherein $R^1$ is lower alkyl and $R^2$ is phenyl, mono- or disubstituted phenyl.

26. The composition of claim 25 employing a compound wherein $R^3$ is dimethylamino.

27. The composition of claim 24 employing a compound wherein $R^1$ is methyl.

28. The composition of claim 24 employing a compound wherein $R^1$ is phenyl, or mono- or disubstituted phenyl and $R^2$ is lower alkyl.

29. The composition of claim 28 employing a compound wherein $R^3$ is dimethylamino.

30. The composition of claim 28 employing a compound wherein $R^2$ is methyl.

31. The composition of claim 30 employing a compound wherein $R^1$ is phenyl, chlorophenyl, methylphenyl, methoxyphenyl, nitrophenyl, or trifluoromethylphenyl.

32. The composition of claim 31 employing a compound wherein $R^1$ is 2-chlorophenyl, 3-chlorophenyl, 4-chlorophenyl, 3-methylphenyl, 4-methylphenyl, 3-nitrophenyl, 4-methoxyphenyl or 3-trifluoromethylphenyl.

33. The composition of claim 24 employing a compound wherein X is O or N—$CH_3$.

* * * * *